United States Patent [19]

Ronchi

[11] Patent Number: 4,900,350
[45] Date of Patent: Feb. 13, 1990

[54] 5-IMINOMETHYL-HALO-ACYLOXAZOLIDINES HAVING AN INHIBITING ACTION ON THE PHYTOTOXICITY OF HERBICIDES

[75] Inventor: Nello Ronchi, Milan, Italy

[73] Assignee: Oxon Italia S.p.A., Pero-Milano, Italy

[21] Appl. No.: 72,240

[22] Filed: Jul. 10, 1987

[30] Foreign Application Priority Data

Jul. 16, 1986 [IT] Italy ............... 21152 A/86

[51] Int. Cl.$^4$ ............ A01N 43/36; A01N 43/40; A01N 43/76; C07D 263/04
[52] U.S. Cl. ............... 71/88; 71/94; 71/95; 540/603; 546/209; 548/215
[58] Field of Search ......... 548/215; 71/88, 94, 71/95; 540/603; 546/209

[56] References Cited

U.S. PATENT DOCUMENTS

| | | | |
|---|---|---|---|
| 2,715,631 | 8/1955 | Croxall et al. | 548/215 |
| 3,959,304 | 5/1976 | Teach | 548/215 |

FOREIGN PATENT DOCUMENTS

| | | | |
|---|---|---|---|
| 136016 | 4/1985 | European Pat. Off. | 548/215 |
| 253291 | 1/1988 | European Pat. Off. | 548/215 |
| 2350547 | 4/1974 | Fed. Rep. of Germany | 548/215 |

OTHER PUBLICATIONS

Teach, Chem. Abst. 95-7257j (1981).
Ronchi, Chem. Abst. 108-163274e (1988).
Gorof et al., Chem. Abst. 95-37104z (1981).
Gorof et al., Chem. Abst. vol. 95-37105a (1981).

*Primary Examiner*—Mukund J. Shah
*Assistant Examiner*—Celilia Shen
*Attorney, Agent, or Firm*—Young & Thompson

[57] ABSTRACT

Compounds of formula:

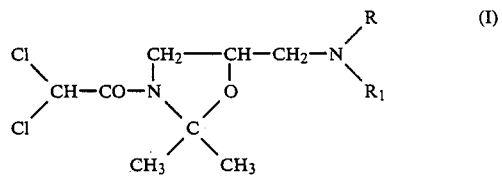

where
R is alkyl having from 1 to 8 carbon atoms, alkenyl having from 3 to 8 carbon atoms or cyclohexyl;
$R_1$ is alkyl having from 1 to 8 carbon atoms, alkenyl having from 3 to 8 carbon atoms or cyclohexyl; and
R and $R_1$ together can form a —(CH$_2$)—$_n$ group wherein n is an integer from 4 to 6. These compounds can be used as phytotoxicity antidotes for thiolcarbamate and/or acetanilide herbicides for use on corn cultivations.

9 Claims, No Drawings

5-IMINOMETHYL-HALO-ACYLOXAZOLIDINES HAVING AN INHIBITING ACTION ON THE PHYTOTOXICITY OF HERBICIDES

BACKGROUND OF THE INVENTION

There are known to be numerous thiolcarbamate and acetanilide herbicides which are highly effective against weeds infesting corn fields. However, these herbicides are frequently phytotoxic towards corn. On the other hand, those infesting weeds most difficult to destroy are not sufficiently controlled by herbicides which are less phytotoxic towards corn, as certain derivatives of the S-triazine or substituted urea families.

It is therefore very important to provide antidotes particularly effective in inhibiting the phytotoxicity of the thiolcarbamates and acetanilides used as selective herbicides for corn.

It is known from literature that various classes of products having this inhibiting action exist. Among the successfully tested compounds described in literature (EP 0021759, or British Patent 2043447) there are variously substituted haloacyloxazolidines.

SUMMARY OF THE INVENTION

The present invention relates to a haloacyloxazolidine family never previously described in literature, namely 5-iminomethyl-halocycloxazolidines, having the general formula:

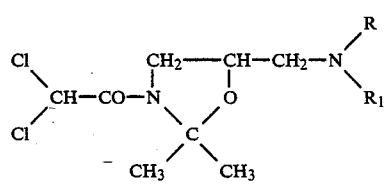

where
R is alkyl having from 1 to 8 carbon atoms, alkenyl, cyclohexyl or arylalkyl;
$R_1$ is alkyl having from 1 to 8 carbon atoms, alkenyl, cyclohexyl or arylalkyl;
R and $R_1$ being apt to form a —$(CH_2)$—$_n$ group.

These compounds are very effective as phytotoxicity antidotes or inhibitors both towards thiolcarbamate herbicides, such as:
  di-propyl-S-ethyl-thiolcarbamate (EPTC)
  di-isobutyl-S-ethyl-thiolcarbamate (Butylate)
  di-propyl-S-propyl-thiolcarbamate (Vernolate),
and towards acetanilide herbicides, such as:
  2-chloro-N-(ethoxymethyl)-2'-methyl-6'-ethylacetanilide (ACETOCHLOR)
  2-chloro-N-(pyrazol-1-yl-methyl)-2', 6'-dimethylacetanilide (METAZACHLOR)

The compounds of formula (I) according to the invention are synthesized in accordance with the following reactions:

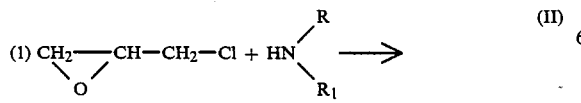

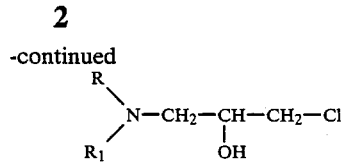

The reaction (1) between epichlorhydrin and secondary amine is carried out in 1–5 hours, at a temperature of between 70° and 100° C., without the need to use solvents.

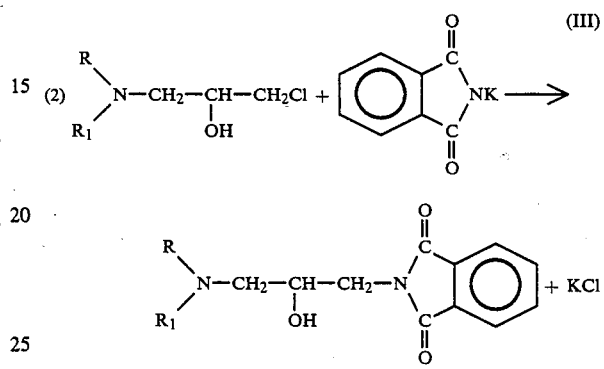

The reaction (2) between compound (II) and potassium phthalimide is carried out in an alcohol at a temperature of between 65° and 80° C., in 5–10 hours.

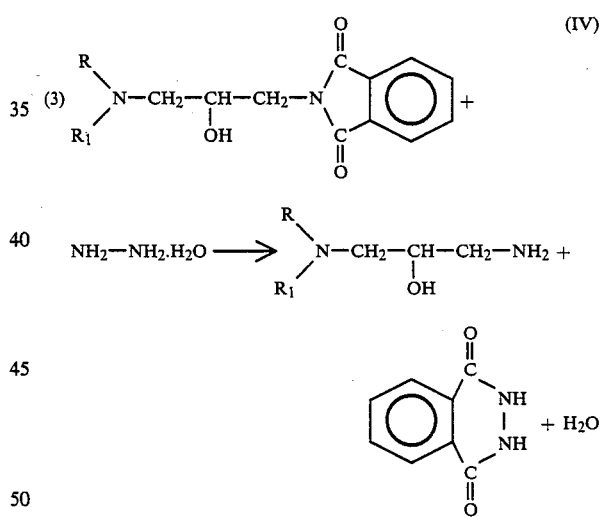

The reaction (3) between compound (III) and hydrazine is carried out in an alcohol at a temperature of between 65° and 80° C. in 2–4 hours.

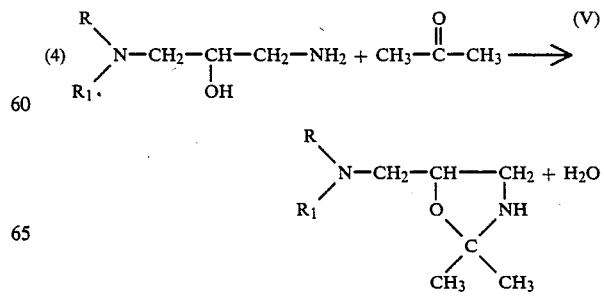

The reaction (4) between compound (IV) and acetone is carried out by azeotropic distillation of the water formed, using an organic solvent apt to form an azeotrope with water.

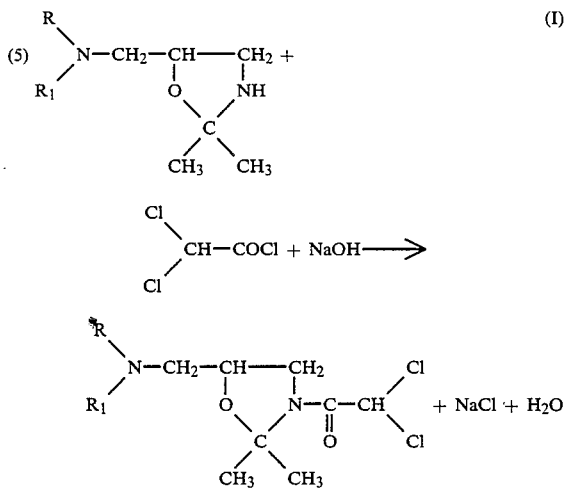

The reaction (5) between compound (V) and dichloroacetyl chloride is carried out in an organic solvent, normally that used in the preceding reaction (4), in the presence of an acid acceptor (NaOH, KOH, tertiary amines or others) at a temperature of between −10° and +10° C. in 15 minutes≈one hour.

DESCRIPTION OF THE PREFERRED EMBODIMENTS

The compounds of formula (I) can be mixed with the aforesaid active herbicide substances to obtain new selective herbicide compositions for corn cultivations.

These herbicide compositions can also contain other selective corn herbicides such as S-triazine herbicides (for example atrazine, simazine, terbutylazine, cyanazine), substituted urea herbicides (for example linuron, metabenzthiazuron), dinitroaniline herbicides (for example pendimethalin), or other herbicides.

These herbicide compositions are obtained by mixing and possibly grinding the active substance with inert substances and adjuvants, and can be formulated either as water-emulsifiable liquids or as fluid suspensions (for example, water-based or organic solvent-based "flowables"). They can also be prepared in the form of granular compounds or as dry or wettable powders. The formulation methods for such herbicide compositions are well known to the expert in the art, as are the type of inert substances (liquids or solids) to be used and the various most suitable adjuvants.

The ratio between antidote compounds of formula (I) and active thiolcarbamate and/or acetanilide herbicide substances, phytotoxic to corn, can vary within very wide limits, but is generally between 1:1 and 1:160.

Herbicide compositions containing compounds of formula (I) with thiolcarbamate and/or acetanilide herbicides can be used before sowing the corn generally by incorporation into the soil by means of suitable equipment, whereas herbicide compositions containing compounds of formula (I) and herbicide acetanilides can also be used on the soil surface after sowing the corn, without further incorporation, but being careful to use them within a few days from sowing (and anyhow before emergence of the infesting weeds, i.e. at their initial appearance on the soil surface).

The aforesaid herbicide compositions are distributed over corn fields by suitable equipment, so as to generally apply a total quantity of herbicides plus antidotes, which may vary from 1 to 17 kg. of active substances per hectare.

A further method of application of the antidote compounds of formula (I) is to treat seed corn before sowing, and then sowing the kernels treated with antidote compounds in fields which have already been deweeded with phytotoxic thiolcarbamate and/or acetanilide herbicides, or in fields which are to be deweeded, after sowing, with phytotoxic acetanilide herbicides.

If used for seed corn treatment, the compounds of formula (I) are formulated in suitable liquid, fluid or powder compositions comprising active substances mixed with inert liquids or solids and/or adjuvants, well known to experts in the art, the compositions containing from 1 to 99% of active substances.

The preparations obtained in this manner are applied to the seed corn by standard equipment available in agriculture, using from 12.5 grams to 400 grams of antidotes per 100 kg of seed corn.

The examples given hereinafter allow to better illustrate the invention, but without limiting it in any way.

PREPARATION EXAMPLE 1

Preparation of 2.2-dimethyl-N-dichloroacetyl-5-diisobutylamino methyl oxazolidine 129.2 g of diisobutylamine are reacted for 3 hours at 80° C. with 101.7 g of epichlorhydrin.

After purifying by distillation, 199.5 g of N-(3-chloro-2-ol) propyl diisobutylamine are obtained. This product is then reacted at 80 ° C. for 10 hours with 166.5 g of potassium phthalimide in 450 ml of anhydrous ethanol. After filtering off the formed potassium chloride, the mass is concentrated and left to crystallize.

261 g of N-(3-diisobutylamino-2-olpropyl) phthalimide are obtained.

The product obtained is hydrolysed by reaction for 3 hours at 80 ° C. in 1600 ml of ethanol with 44.1 g of hydrazine monohydrate.

After acidification with hydrochloric acid, the ethyl alcohol is distilled off, adding water. The phthalhydrazide is separated by filtration. The 3-diisobutyl-2-ol-propylamine is recovered from the mother liquors by alkalising with NaOH and extracting with toluene.

After drying the toluenic mass, 91 g of acetone are added and the mixture is heated to boiling, azeotropically distilling off the water formed in the reaction.

In this manner a toluenic solution of 0,2-dimethyl-5-diisobutylaminoethyl oxazolidine is obtained, which is reacted with 121 g of dichloroacetylchloride and 110 g of 30% NaOH, at 0°–5° C., for 30 minutes.

Water is added to dissolve the sodium chloride formed. The organic layer is separated from the aqueous layer, and the solvent is removed by distillation to obtain 235 g of 2,2-dimethyl-3-dichloroacetyl -5-diisobutylamino methyl oxazolidine, in the form of a yellow-brown oil partially solid at ambient temperature.

The IR, NMR, elementary and gas chromatography analyses have confirmed the structure of the product obtained. This product is indicated hereinafter by the code number 0134.

PREPARATION EXAMPLES 2-9 the following products were synthesized using the method described in Example 1:

2,2-dimethyl-3-dichloroacetyl-5-ethyl cyclohexylaminomethyl oxazolidine 200.1 g obtained (code number: 0.135)

2,2-dimethyl-3-dichloroacetyl-5-dimethylamino methyl oxazolidine 248.5 g obtained (code number: 0 170)

2,2-dimethyl-3-dichloroacetyl-5-di-n-octylamino methyl oxazolidine 238.8 g obtained (code number: 0 171)

2,2-dimethyl-3-dichloroacetyl-5-di-n-propylamino methyl oxazolidine 139.8 g obtained (code number: 0 187)

2,2-dimethyl-3-dichloroacetyl-5-di-sec-butylamino methyl oxazolidine 215.4 g obtained (code number: 0 182)

2,2-dimethyl-3-dichloroacetyl-5-diallylamino methyl oxazolidine 77.04 g obtained (code number: 0 186)

FORMULATION EXAMPLE 1

The following substances are mixed together in a liquid mixer

| Technical EPTC 95% | 758 g |
| --- | --- |
| Technical 0 134 95% | 63 g |
| SOITEM* 115 | 100 g |
| Solvent naphtha | to make up to 1 liter |

*Emulsifier produced by SOITEM - Milan

A water-emulsifiable liquid is obtained, suitable for use as a herbicide in corn fields, for pre-sowing application by incorporation into the soil.

(*) Emulsifier produced by SOITEM - Milan

FORMULATION EXAMPLE 2

The following substances are mixed together:

| Technical butylate 96% | 750 g |
| --- | --- |
| Technical 0 134 95% | 32 g |
| GERONOL* FF4E | 75 g |
| Solvent naphtha | to make up to 1 liter |

*Emulsifier produced by GERONAZZO - Milan

A water-emulsifiable liquid herbicide composition is obtained, for pre-sowing application to maize fields by incorporation.

(*) Emulsifier produced by GERONAZZO - Milan

FORMULATION EXAMPLE 3

The following substances are mixed together:

| Technical acetochlor 95% | 532 g |
| --- | --- |
| Technical 0 134 95% | 53 g |
| SOITEM* 999 | 20 g |
| SOITEM* 101 | 30 g |
| monochlorobenzene | to make up to 1 liter |

*Emulsifiers produced by SOITEM - Milan

A water-emulsifiable liquid herbicide is obtained for pre-sowing or post-sowing application, but before appearance of infesting weeds in corn fields.

(*) Emulsifiers produced by SOITEM - Milan

FORMULATION EXAMPLE 4

The following are mixed together:

| Technical 0 134 95% | 263 g |
| --- | --- |
| GERONOL* FF4E | 100 g |
| xylol | to make up to 1 liter |

*Emulsifier produced by GERONAZZO - Milan

A water-emulsifiable liquid is obtained, which can be used for seed corn treatment.

Analogous compositions can be obtained using the compounds of Preparation Examples 2-9.

APPLICATION EXAMPLE 1

Aqueous emulsions of the herbicides indicated in the following Table A are distributed over plastic bowls containing sandy loam soil, the emulsions being mixed before use with aqueous emulsions of compounds of formula (I), prepared in accordance with the preceding Formulation Examples, the quantities being widely varied.

After distributing the mixtures of herbicides and compounds of formula (I), these products are incorporated by being mixed with the soil to a depth of 10 cm.

ALBION corn is then sown together with infesting weed seeds, the bowls being then kept in a greenhouse at temperatures suited for corn and weed growth, irrigating every two days.

30 days after sowing, one observes the phytotoxicity level on the corn and weed growths emerging from the soil, said level being considered by the E.W.R.S. (European Weed Research Society) scale, as follows:

| Level 1 = no phytotoxicity, healthy plants |
| --- |
| Level 2 = about 2.5% phytotoxicity |
| Level 3 = about 5% phytotoxicity |
| Level 4 = about 10% phytotoxicity |
| Level 5 = about 15% phytotoxicity |
| Level 6 = about 25% phytotoxicity |
| Level 7 = about 35% phytotoxicity |
| Level 8 = about 62.5% phytotoxicity |
| Level 9 = plants totally destroyed. |

In the following Table A, the infesting weeds considered are:

1. *Echinochloa crus galli*
2. *Setaria viridis*
3. *Amaranthus retroflexus*
4. *Chenopodium album*

TABLE A

Results of phytotoxicity levels 1-9, observed 30 days after sowing—by the E.W.R.S. method—on ALBION corn and various infesting weeds sown on soil treated with various mixtures of herbicides and compounds of formula (I).

| Herbicide | Quantity kg/ha | Com-form. I | Quantity kg/ha | Corn | 1. | 2. | 3. | 4. |
| --- | --- | --- | --- | --- | --- | --- | --- | --- |
| EPTC | 16+ | 0 134 | 1.6 | 1 | 9 | 9 | 9 | 9 |
| EPTC | 16+ | 0 134 | 0.4 | 1 | 9 | 9 | 9 | 9 |
| EPTC | 16+ | 0 134 | 0.1 | 2 | 9 | 9 | 9 | 9 |

Phytotoxicity 1-9 E.W.R.S. Infesting weeds

-continued

| Herbicide | Quantity kg/ha | Com-form. I | Quantity kg/ha | Corn | Infesting weeds 1. | 2. | 3. | 4. |
|---|---|---|---|---|---|---|---|---|
| EPTC | 16+ | 0 135 | 1.6 | 1 | 9 | 9 | 9 | 9 |
| EPTC | 16+ | 0 135 | 0.4 | 1 | 9 | 9 | 9 | 9 |
| EPTC | 16+ | 0 135 | 0.1 | 3 | 9 | 9 | 9 | 9 |
| EPTC | 16+ | 0 187 | 1.6 | 1 | 9 | 9 | 9 | 9 |
| EPTC | 16+ | 0 187 | 0.4 | 2 | 9 | 9 | 9 | 9 |
| EPTC | 16+ | 0 187 | 0.1 | 3 | 9 | 9 | 9 | 9 |
| EPTC | 16 | — | — | 8 | 9 | 9 | 9 | 9 |
| EPTC | 8+ | 0 134 | 1.6 | 1 | 9 | 9 | 9 | 9 |
| EPTC | 8+ | 0 134 | 0.4 | 1 | 9 | 9 | 9 | 9 |
| EPTC | 8+ | 0 134 | 0.1 | 1 | 9 | 9 | 9 | 9 |
| EPTC | 8+ | 0 135 | 1.6 | 1 | 9 | 9 | 9 | 9 |
| EPTC | 8+ | 0 135 | 0.4 | 1 | 9 | 9 | 9 | 9 |
| EPTC | 8+ | 0 135 | 0.1 | 2 | 9 | 9 | 9 | 9 |
| EPTC | 8+ | 0 187 | 1.6 | 1 | 9 | 9 | 9 | 9 |
| EPTC | 8+ | 0 187 | 0.4 | 1 | 9 | 9 | 9 | 9 |
| EPTC | 8+ | 0 187 | 0.1 | 2 | 9 | 9 | 9 | 9 |
| EPTC | 8 | — | — | 7 | 9 | 9 | 9 | 9 |
| BUTYLATE | 8+ | 0 134 | 1.6 | 1 | 9 | 9 | 9 | 9 |
| BUTYLATE | 8+ | 0 134 | 0.4 | 1 | 9 | 9 | 9 | 9 |
| BUTYLATE | 8+ | 0 134 | 0.1 | 1 | 9 | 9 | 9 | 9 |
| BUTYLATE | 8+ | 0 135 | 1.6 | 1 | 9 | 9 | 9 | 9 |
| BUTYLATE | 8+ | 0 135 | 0.4 | 1 | 9 | 9 | 9 | 9 |
| BUTYLATE | 8+ | 0 135 | 0.1 | 1 | 9 | 9 | 9 | 9 |
| BUTYLATE | 8+ | 0 187 | 1.6 | 1 | 9 | 9 | 9 | 9 |
| BUTYLATE | 8+ | 0 187 | 0.4 | 1 | 9 | 9 | 9 | 9 |
| BUTYLATE | 8+ | 0 187 | 0.1 | 1 | 9 | 9 | 9 | 9 |
| BUTYLATE | 8 | — | — | 5 | 9 | 9 | 9 | 9 |
| VERNOLATE | 8+ | 0 134 | 1.6 | 1 | 9 | 9 | 9 | 9 |
| VERNOLATE | 8+ | 0 134 | 0.4 | 1 | 9 | 9 | 9 | 9 |
| VERNOLATE | 8+ | 0 134 | 0.1 | 2 | 9 | 9 | 9 | 9 |
| VERNOLATE | 8 | — | — | 6 | 9 | 9 | 9 | 9 |
| ACETOCHLOR | 4+ | 0 134 | 1.6 | 1 | 9 | 9 | 9 | 9 |
| ACETOCHLOR | 4+ | 0 134 | 0.4 | 2 | 9 | 9 | 9 | 9 |
| ACETOCHLOR | 4+ | 0 134 | 0.1 | 3 | 9 | 9 | 9 | 9 |
| ACETOCHLOR | 4+ | 0 135 | 1.6 | 1 | 9 | 9 | 9 | 9 |
| ACETOCHLOR | 4+ | 0 135 | 0.4 | 3 | 9 | 9 | 9 | 9 |
| ACETOCHLOR | 4+ | 0 135 | 0.1 | 4 | 9 | 9 | 9 | 9 |
| ACETOCHLOR | 4+ | 0 187 | 1.6 | 2 | 9 | 9 | 9 | 9 |
| ACETOCHLOR | 4+ | 0 187 | 0.4 | 2 | 9 | 9 | 9 | 9 |
| ACETOCHLOR | 4+ | 0 187 | 0.1 | 4 | 9 | 9 | 9 | 9 |
| ACETOCHLOR | 4 | — | — | 6 | 9 | 9 | 9 | 9 |
| ACETOCHLOR | 2+ | 0 134 | 1.6 | 1 | 9 | 9 | 9 | 9 |
| ACETOCHLOR | 2+ | 0 134 | 0.4 | 1 | 9 | 9 | 9 | 9 |
| ACETOCHLOR | 2+ | 0 134 | 0.1 | 2 | 9 | 9 | 9 | 9 |
| ACETOCHLOR | 2+ | 0 135 | 1.6 | 2 | 9 | 9 | 9 | 9 |
| ACETOCHLOR | 2+ | 0 135 | 0.4 | 3 | 9 | 9 | 9 | 9 |
| ACETOCHLOR | 2+ | 0 135 | 0.1 | 3 | 9 | 9 | 9 | 9 |
| ACETOCHLOR | 2+ | 0 187 | 1.6 | 1 | 9 | 9 | 9 | 9 |
| ACETOCHLOR | 2+ | 0 187 | 0.4 | 2 | 9 | 9 | 9 | 9 |
| ACETOCHLOR | 2+ | 0 187 | 0.1 | 3 | 9 | 9 | 9 | 9 |
| ACETOCHLOR | 2 | — | — | 5 | 9 | 9 | 9 | 9 |
| Untreated blank sample | — | — | — | 1 | 1 | 1 | 1 | 1 |

The results reported in Table A clearly indicate that mixtures of formula (I) compounds with herbicides, which are normally phytotoxic towards corn when not containing the formula (I) compounds, eliminate maize phytotoxicity or reduce it to negligible levels, without reducing effectiveness towards weeds.

APPLICATION EXAMPLE 2

In plastic bowls containing sandy loam soil—kept in a greenhouse and irrigated every two days—one sows corn of the DEKALB XL 69 variety and seeds of various infesting weeds, and the next day the soil surface is sprayed with mixtures of aqueous acetochlor emulsions and aqueous emulsions of formula (I) compounds, prepared in accordance with the preceding Formulation Examples, the quantities being widely varied.

30 days after sowing, the phytotoxicity 1-9 towards corn and infesting weeds is considered by the E.W.R.S. method (as described in detail in the preceding example). The results observed are reported in the following Table B, in which the compound code numbers have the same meaning as in the preceding Table A.

TABLE B

Phytotoxicity 1-9 considered by the E.W.R.S. method 30 days after sowing, having used herbicide mixtures of acetochlor and formula (I) compounds one day after sowing.

| Herbicide | Quantity kg/ha | Com-form. I | Quantity kg/ha | Corn | Infesting weeds 1. | 2. | 3. | 4. |
|---|---|---|---|---|---|---|---|---|
| ACETOCHLOR | 2+ | 0 134 | 1.6 | 1 | 9 | 9 | 9 | 9 |
| ACETOCHLOR | 2+ | 0 134 | 0.4 | 1 | 9 | 9 | 9 | 9 |
| ACETOCHLOR | 2+ | 0 134 | 0.1 | 3 | 9 | 9 | 9 | 9 |
| ACETOCHLOR | 2+ | 0 135 | 1.6 | 1 | 9 | 9 | 9 | 9 |

-continued

| Herbicide | Quantity kg/ha | Com-form. I | Quantity kg/ha | Phytotoxicity 1-9 E.W.R.S. |  |  |  |  |
|---|---|---|---|---|---|---|---|---|
|  |  |  |  | Corn | 1. | 2. | 3. | 4. |
| ACETOCHLOR | 2+ | 0 135 | 0.4 | 2 | 9 | 9 | 9 | 9 |
| ACETOCHLOR | 2+ | 0 135 | 0.1 | 4 | 9 | 9 | 9 | 9 |
| ACETOCHLOR | 2+ | 0 187 | 1.6 | 1 | 9 | 9 | 9 | 9 |
| ACETOCHLOR | 2+ | 0 187 | 0.4 | 1 | 9 | 9 | 9 | 9 |
| ACETOCHLOR | 2+ | 0 187 | 0.1 | 3 | 9 | 9 | 9 | 9 |
| ACETOCHLOR | 2 | — | — | 6 | 9 | 9 | 9 | 9 |
| ACETOCHLOR | 1+ | 0 134 | 1.6 | 1 | 9 | 9 | 9 | 9 |
| ACETOCHLOR | 1+ | 0 134 | 0.4 | 1 | 9 | 9 | 9 | 9 |
| ACETOCHLOR | 1+ | 0 134 | 0.1 | 1 | 9 | 9 | 9 | 9 |
| ACETOCHLOR | 1+ | 0 135 | 1.6 | 1 | 9 | 9 | 9 | 9 |
| ACETOCHLOR | 1+ | 0 135 | 0.4 | 1 | 9 | 9 | 9 | 9 |
| ACETOCHLOR | 1+ | 0 135 | 0.1 | 3 | 9 | 9 | 9 | 9 |
| ACETOCHLOR | 1+ | 0 187 | 1.6 | 1 | 9 | 9 | 9 | 9 |
| ACETOCHLOR | 1+ | 0 187 | 0.4 | 1 | 9 | 9 | 9 | 9 |
| ACETOCHLOR | 1+ | 0 187 | 0.1 | 2 | 9 | 9 | 9 | 9 |
| ACETOCHLOR | — | — | — | 5 | 9 | 9 | 9 | 9 |
| METAZACHLOR | 1+ | 0 134 | 1.6 | 1 | 9 | 9 | 9 | 9 |
| METAZACHLOR | 1+ | 0 134 | 0.4 | 1 | 9 | 9 | 9 | 9 |
| METAZACLOR | 1+ | 0 134 | 0.1 | 2 | 9 | 9 | 9 | 9 |
| METAZACLOR | 1 | — | — | 6 | 9 | 9 | 9 | 9 |

The results reported in Table B clearly indicate that compounds of formula (I) eliminate phytotoxicity of ACETOCHLOR or reduce it to negligible levels when used after sowing, but before appearance of the corn and infesting weeds, without reducing the effectiveness of the herbicide towards weeds.

APPLICATION EXAMPLE 3

Aqueous emulsions of herbicides phytotoxic towards corn are distributed in various quantities—as reported in the following Table C—over plastic bowls containing sandy loam soil, in which infesting weed seeds have been placed, said herbicides being then incorporated into the soil to a depth of 10 cm.

Seed corn of the ISCHIA variety is separately treated with aqueous emulsions of formula (I) compounds, prepared as indicated in the preceding Formulation Examples, using decreasing quantities of compounds per weight unit of seed corn.

These kernels, treated with antidote compounds, are sown in the bowls treated with the various herbicides, and the phytotoxicity 1-9 towards corn and weeds is considered after 30 days by the E.W.R.S. method (as described in detail in Application Example 1).

The results observed are reported in the following Table C, in which the compound code numbers have the same meaning as in Tables A and B.

TABLE C

Phytotoxicity 1-9 considered by the E.W.R.S. method, 30 days after sowing, using herbicide mixtures of acetochlor and formula (I) compounds one day after sowing.

| Herbicide | Quantity kg/ha | Com-form. I | Quantity kg/ha | Phytotoxicity 1-9 E.W.R.S. |  |  |  |  |
|---|---|---|---|---|---|---|---|---|
|  |  |  |  | Corn | 1. | 2. | 3. | 4. |
| EPTC | 16+ | 0 134 | 0.4 | 1 | 9 | 9 | 9 | 9 |
| EPTC | 16+ | 0 134 | 0.2 | 1 | 9 | 9 | 9 | 9 |
| EPTC | 16+ | 0 134 | 0.05 | 1 | 9 | 9 | 9 | 9 |
| EPTC | 16+ | 0 134 | 0.0125 | 2 | 9 | 9 | 9 | 9 |
| EPTC | 16+ | 0 135 | 0.2 | 1 | 9 | 9 | 9 | 9 |
| EPTC | 16+ | 0 135 | 0.05 | 2 | 9 | 9 | 9 | 9 |
| EPTC | 16+ | 0 135 | 0.0125 | 3 | 9 | 9 | 9 | 9 |
| EPTC | 16+ | 0 187 | 0.2 | 1 | 9 | 9 | 9 | 9 |
| EPTC | 16+ | 0 187 | 0.05 | 2 | 9 | 9 | 9 | 9 |
| EPTC | 16+ | 0 187 | 0.0125 | 4 | 9 | 9 | 9 | 9 |
| EPTC | 16 | — | — | 8 | 9 | 9 | 9 | 9 |
| EPTC | 8+ | 0 134 | 0.2 | 1 | 9 | 9 | 9 | 9 |
| EPTC | 8+ | 0 134 | 0.05 | 1 | 9 | 9 | 9 | 9 |
| EPTC | 8+ | 0 134 | 0.0125 | 1 | 9 | 9 | 9 | 9 |
| EPTC | 8+ | 0 135 | 0.2 | 1 | 9 | 9 | 9 | 9 |
| EPTC | 8+ | 0 135 | 0.05 | 1 | 9 | 9 | 9 | 9 |
| EPTC | 8+ | 0 135 | 0.0125 | 1 | 9 | 9 | 9 | 9 |
| EPTC | 8+ | 0 187 | 0.2 | 1 | 9 | 9 | 9 | 9 |
| EPTC | 8+ | 0 187 | 0.05 | 2 | 9 | 9 | 9 | 9 |
| EPTC | 8+ | 0 187 | 0.0125 | 3 | 9 | 9 | 9 | 9 |
| EPTC | 8 | — | — | 7 | 9 | 9 | 9 | 9 |
| BUTYLATE | 8+ | 0 134 | 0.2 | 1 | 9 | 9 | 9 | 9 |
| BUTYLATE | 8+ | 0 134 | 0.05 | 1 | 9 | 9 | 9 | 9 |
| BUTYLATE | 8+ | 0 134 | 0.0125 | 1 | 9 | 9 | 9 | 9 |
| BUTYLATE | 8+ | 0 135 | 0.2 | 1 | 9 | 9 | 9 | 9 |
| BUTYLATE | 8+ | 0 135 | 0.05 | 1 | 9 | 9 | 9 | 9 |
| BUTYLATE | 8+ | 0 135 | 0.0125 | 2 | 9 | 9 | 9 | 9 |
| BUTYLATE | 8+ | 0 187 | 0.2 | 1 | 9 | 9 | 9 | 9 |
| BUTYLATE | 8+ | 0 187 | 0.05 | 1 | 9 | 9 | 9 | 9 |
| BUTYLATE | 8+ | 0 187 | 0.0125 | 2 | 9 | 9 | 9 | 9 |
| BUTYLATE | 8 | — | — | 4 | 9 | 9 | 9 | 9 |
| VERNOLATE | 8+ | 0 134 | 0.2 | 1 | 9 | 9 | 9 | 9 |
| VERNOLATE | 8+ | 0 134 | 0.05 | 1 | 9 | 9 | 9 | 9 |
| VERNOLATE | 8+ | 0 134 | 0.0125 | 2 | 9 | 9 | 9 | 9 |
| VERNOLATE | 8 | — | — | 6 | 9 | 9 | 9 | 9 |
| ACETOCHLOR | 4+ | 0 134 | 0.4 | 1 | 9 | 9 | 9 | 9 |
| ACETOCHLOR | 4+ | 0 134 | 0.2 | 1 | 9 | 9 | 9 | 9 |
| ACETOCHLOR | 4+ | 0 134 | 0.05 | 1 | 9 | 9 | 9 | 9 |
| ACETOCHLOR | 4+ | 0 134 | 0.0125 | 2 | 9 | 9 | 9 | 9 |
| ACETOCHLOR | 4+ | 0 135 | 0.2 | 1 | 9 | 9 | 9 | 9 |
| ACETOCHLOR | 4+ | 0 135 | 0.05 | 2 | 9 | 9 | 9 | 9 |
| ACETOCHLOR | 4+ | 0 135 | 0.0125 | 4 | 9 | 9 | 9 | 9 |
| ACETOCHLOR | 4+ | 0 187 | 0.2 | 1 | 9 | 9 | 9 | 9 |
| ACETOCHLOR | 4+ | 0 187 | 0.05 | 1 | 9 | 9 | 9 | 9 |

-continued

| Herb-icide | Quantity kg/ha | Com-form. I | Quantity kg/ha | Corn | 1. | 2. | 3. | 4. |
|---|---|---|---|---|---|---|---|---|
| CHLOR ACETO-CHLOR | 4+ | 0 187 | 0.0125 | 3 | 9 | 9 | 9 | 9 |
| ACETO-CHLOR | 4 | — | — | 7 | 9 | 9 | 9 | 9 |
| ACETO-CHLOR | 2+ | 0 134 | 0.2 | 1 | 9 | 9 | 9 | 9 |
| ACETO-CHLOR | 2+ | 0 134 | 0.05 | 1 | 9 | 9 | 9 | 9 |
| ACETO-CHLOR | 2+ | 0 134 | 0.0125 | 1 | 9 | 9 | 9 | 9 |
| ACETO-CHLOR | 2+ | 0 135 | 0.2 | 1 | 9 | 9 | 9 | 9 |
| ACETO-CHLOR | 2+ | 0 135 | 0.05 | 1 | 9 | 9 | 9 | 9 |
| ACETO-CHLOR | 2+ | 0 135 | 0.0125 | 2 | 9 | 9 | 9 | 9 |
| ACETO-CHLOR | 2+ | 0 187 | 0.2 | 1 | 9 | 9 | 9 | 9 |
| ACETO-CHLOR | 2+ | 0 187 | 0.05 | 1 | 9 | 9 | 9 | 9 |
| ACETO-CHLOR | 2+ | 0 187 | 0.0125 | 2 | 9 | 9 | 9 | 9 |
| ACETO-CHLOR | 2 | — | — | 5 | 9 | 9 | 9 | 9 |

The results reported in Table C clearly indicate that the compounds of formula (I), when applied directly to maize seeds, eliminate or reduce to negligible levels the phytotoxicity of thiolcarbamate or acetanilide herbicides used before corn sowing and incorporated into the soil, without reducing their effectiveness towards weeds.

What is claimed:

1. Compounds of the formula:

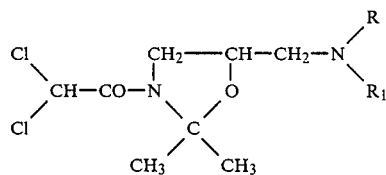

wherein R is alkyl having from 1 to 8 carbon atoms, allyl having from 3 to 8 carbon atoms or cyclohexyl;
R1 is alkyl having from 1 to 8 carbon atoms, allyl having from 3 to 8 carbon atoms or cyclohexyl, or R and $R_1$ together form a —(CH2)—$_n$ group in which n is an integer from 4 to 6.

2. A selective herbicide composition for corn, comprising a herbicidally effective amount of at least one compound as claimed in claim 1, in admixture with thiolcarbamate and/or acetanilide herbicides and inert substances.

3. A composition as claimed in claim 2, wherein said compound is 2,2-dimethyl-3-dichloroacetyl-5-diisobutylamino methyl oxazolidine, and the herbicide is di-propyl-S-ethyl-thiolcarbamate.

4. A composition as claimed in claim 2, wherein said compound is 2,2-dimethyl-3-dichloroacetyl-5-diisobutylamino methyl oxazolidine, and the herbicide is di-isobutyl-S-ethyl-thiolcarbamate.

5. A composition as claimed in claim 2, wherein said compound is 2,2-dimethyl-3-dichloroacetyl-5-diisobutylamino methyl oxazolidine, and the herbicide is 2-chloro-N-(ethoxymethyl)-2'-methyl-6'-ethyl acetanilide.

6. A composition as claimed in claim 2, wherein the ratio between the compound of claim 1 and thiolcarbamate and/or acetanilide herbicides is between 1:1 and 1:160.

7. A method for the selective deweeding of corn cultivations, comprising using in quantities varying from 1 to 17 kg/ha of active substance a herbicide composition as claimed in claim 2.

8. A seed corn treatment composition, containing from 1 to 99% by weight of at least one compound as claimed in claim 1, in admixture with an agriculturally acceptable excipient.

9. A method for deweeding corn fields by using thiolcarbamate and/or acetanilide herbicides which are phytotoxic towards corn, together with seed corn treated with a composition as claimed in claim 8 in quantities of between 12.5 g and 400 g per 100 kg of seed corn.

* * * * *